United States Patent [19]

van den Bosch et al.

[11] Patent Number: 5,780,617
[45] Date of Patent: Jul. 14, 1998

[54] SYNTHESIS OF LIPONUCLEOTIDES

[75] Inventors: Henk van den Bosch, Maarn; Gysbert M. T. van Wijk, Utrecht, both of Netherlands; Raj Kumar, San Diego; Karl Y. Hostetler, Del Mar, both of Calif.

[73] Assignee: NeXstar Pharmaceuticals, Inc., Boulder, Colo.

[21] Appl. No.: 251,018

[22] Filed: May 31, 1994

Related U.S. Application Data

[63] Continuation of Ser. No. 706,873, May 29, 1991, abandoned, which is a continuation of Ser. No. 530,556, May 29, 1990, abandoned.

[51] Int. Cl.$^6$ .............................. C07H 1/02; C07F 9/02; C07F 9/06; C07F 9/28
[52] U.S. Cl. ................. 536/55.3; 536/26.71; 536/26.72; 558/127; 558/132
[58] Field of Search .............................. 536/27.12, 26.1, 536/26.2, 55.3, 26.71, 26.72; 558/127, 132

[56] References Cited

U.S. PATENT DOCUMENTS

| | | | |
|---|---|---|---|
| 4,291,024 | 9/1981 | Turcotte | 536/27 |
| 4,622,392 | 11/1986 | Hong et al. | 536/27 |
| 4,797,479 | 1/1989 | Shuto et al. | 536/27 |
| 4,921,951 | 5/1990 | Shuto et al. | 536/27 |

FOREIGN PATENT DOCUMENTS

| | | |
|---|---|---|
| 2168350 | 6/1986 | United Kingdom |
| 8600309 | 1/1986 | WIPO |

OTHER PUBLICATIONS ter Schegget, et al., Biochim. Biophys. Acta. 239:234–242 (1971).
Poorthius, et al., Biochim. Biophys. Acta 431:408–415 (1976).
Raetz, et al., Science 196, 303–305 (1977).
Turcotte, et al., Biochim. Biophys. Acta, 619: 604–618 (1980).
Matsushita, et al., Cancer Research 41:2702–2713 (1981).
Paulus, et al., J. Biol. Chem. 235, 1303 (1960).
Agranoff, et al., Biochem. Prep. 10, 47–51 (1963).
Carmen, et al., J. Food Biochem. 4, 53–59 (1980).
Hong, et al., J. Med. Chem. 33, 1380–1386 (1990).
Kates, et al., Methods in Enzymology 14, 197–203 (1969).
Lapidot, et al., Chem. Phys. Lipids 3, 125 (1969).
Eibl, et al. Biochim. Biophys. Acta 553, 476 (1979).
Heinz, et al., Eur. J. Biochem. 184, 445 (1989).
Yoshikawa, et al., Tetrahedron Lett. 50, 5065–5068 (1967).
Yoshikawa, et al., Bull. Chem. Soc. Japan 42, 3505–3508 (1967).
Bligh, et al., Can. J. Biochem. 37:911–917 (1959).
Geurts VanKessel, et al., Biochim. Biophys. Acta 486, 524–530 (1977).
Prottey, et al., Biochem. J. 105:379–391 (1967).
MacCross, et al., Biochem. Biophys. Res. Commun., 85 (2):714–723 (1978).
Ryu, et al., J. Med. Chem., 25:1322–1329 (1982).
Roseman, et al., J. Amer. Chem. Soc. 83:659–675 (1961).
Shapiro, B., Biochem. J. 53:663 (1953).
Chang, et al., J. Biol. Chem. 242:516–519 (1967).
Rouser, et al., Lipids 5, 494–496 (1970).

*Primary Examiner*—Gary L. Kunz
*Attorney, Agent, or Firm*—Swanson & Bratschun

[57] ABSTRACT

A process for the preparation of glycerol di- or triphosphate derivatives comprising coupling the phosphate group of a glycerol monophosphate derivative in which one of the phosphate hydroxyls is replaced by a leaving group, with the terminal phosphate group of a mono- or diphosphate compound or a salt thereof, in the presence of a basic catalyst, under anhydrous conditions.

24 Claims, 4 Drawing Sheets

SYNTHESIS OF LIPONUCLEOTIDES

RELATED APPLICATIONS

This application is a continuation of application Ser. No. 07/706,873, filed May 29, 1991 now abandoned, which is a continuation of application Ser. No. 530,556, filed May 29, 1990 now abandoned.

This application is related to U.S. Ser. No. 373,088, filed Jun. 28, 1989, now U.S. Pat. No. 5,223,263, which is a continuation in part of U.S. Ser. No. 216,412, filed Jul. 7, 1988 now abandoned, and U.S. Ser. No. 319,485, filed Mar. 6, 1989 now abandoned. This application is further related to U.S. Ser. No. 440,898, filed Nov. 22, 1989 now U.S. Pat. No. 5,195,654. The disclosures of these applications are hereby expressly incorporated by reference.

FIELD OF THE INVENTION

The present invention relates to an improved chemical synthesis for the preparation of biologically important compounds. More particularly, the present invention concerns an improved method for the synthesis of glycerol di- and triphosphate derivatives, preferably nucleoside di- and triphosphate esters of glycerol lipids, such as nucleoside diphosphate mono- and diglycerides. The glycerol monophosphate amidate intermediates of the new synthesis are novel compounds.

BACKGROUND OF THE INVENTION

Figure 1:
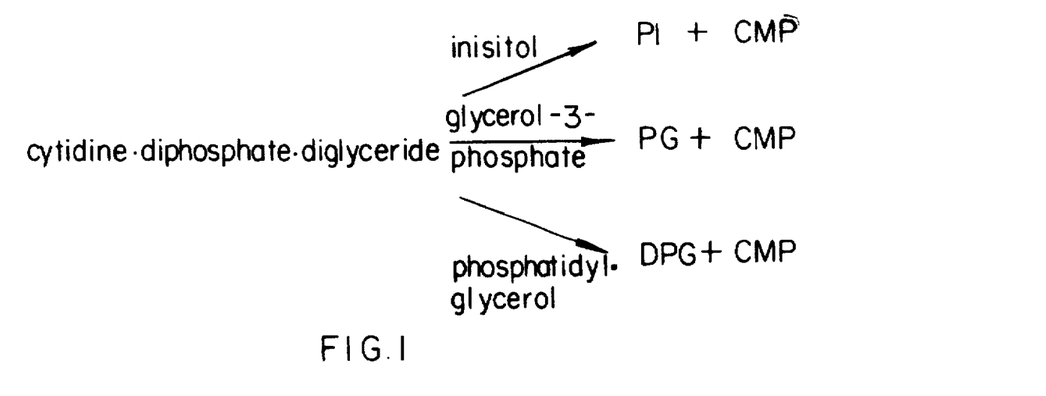
FIG. 1 illustrates the biosynthesis of phosphatidylinositol (PI), phosphatidylglycerol (PG) and cardiolipin in mammals via the CDP-DG pathway. All three conversions give rise to the release of cytidine-5'-monophosphate (CMP).

Nucleoside di- and triphosphate esters of glycerol and glycerol derivatives are known in the art. Among them, nucleoside diphosphate diglycerides are of particular importance due to their role in biochemical processes. The synthesis and the biological importance of a naturally-occurring liponucleotide, cytidine diphosphate diglyceride (CDP-DG) in lipid biosynthesis have been well documented since the early 1960's. In eukaryotes, CDP-DG is a precursor of phosphatidylglycerol, cardiolipin and phosphatidylinositol (FIG. 1), while in prokaryotes it is converted to phosphatidylserine and phosphatidylglycerophosphate. All of these reactions proceed with the concomitant release of the nucleotide, cytidine-5'-monophosphate. However, the specificity of the enzymes involved in these conversions is not restricted to the CDP-DG substrate. It has been shown that also 2'-deoxycytidine, adenosine, guanosine and uridine analogues can serve as activated phosphatidic acid donors in the biosynthetic pathways illustrated in FIG. 1 [Ter Schegget et al., *Biochim. Biophys. Acta* 239, 234–243 (1971); Poorthuis et al., *Biochim. Biophys. Acta* 431, 408–415 (1976)].

The chemical synthesis of a CDP-DG analog (ara-CDP-DL-dipalmitin), in which the anti-neoplastic agent cytosine arabinoside (ara-C) was substituted for the cytidine moiety, has been reported by Raetz et al., *Science* 196, 303–305 (1977). It was shown that this phospholipid prodrug of ara-C was metabolized in a manner analogous to CDP-DG itself in that enzymes in rat and human liver converted this analog to phosphatidylinositol, thereby releasing ara-C-5'-monophosphate (ara-CMP). Although ara-C is a potent antitumor agent, its use in cancer therapy is limited by the activity of the kinase present in the mammalian tissues that is required for its conversion to ara-CMP. Similarly, the efficacy of other clinically used anti-neoplastic pyrimidine nucleosides, for example 5-fluorouracil, 5-fluorodeoxyuridine, and 6-azauridine, is limited by kinase activity. Since the release of ara-CMP from ara-CDP-DL-dipalmitin during phosphatidylinositol synthesis is independent of kinase activity, administration of ara-C and analogous compounds in the form of phospholipid prodrugs is expected to enhance anti-tumor activity, and lower toxicity.

The synthesis of several CDP-DG analogs containing the cytosine-1-β-D-arabinofuranosyl (ara-C) moiety, as potential antitumor drugs, has been reported by Turcotte et al., *Biochem. Biophys. Acta* 619, 604–618 (1980).

Matsushita et al. synthesized nucleoside 5'-diphosphate-L-1,2-dipalmitin derivatives of 1-β-D-arabinofuranosylcytosine (ara-C), 9-β-D-arabinofuranosyladenine (ara-A), and tubercidin (TU). The nucleotides ara-C, ara-A and TU are known chemotherapeutic agents for treatment of various types of cancer.

The chemical synthesis, characterization and biological activity of lipid derivatives of antiviral nucleosides, including several CDP-DG analogs with antiretroviral activity, are disclosed in the copending patent application U.S. Ser. No. 373,088, filed Jun. 28, 1989, assigned to Vical, Inc. In these analogs the cytidine part of CDP-DG was, for example, replaced by 3'-deoxythymidine (3dT), 3'-azido-3'-deoxythymidine (AZT) or 2', 3'-dideoxycytidine (ddC). These compounds are potent inhibitors of the human immunodeficiency virus (HIV), the causative agent of acquired immunodeficiency syndrome (AIDS). The application additionally discloses a large number of other antiviral phosphatidylnucleosides and nucleoside diphosphate mono- and diglycerides, as well as methods for their synthesis.

The chemical synthesis of CDP-DG in low yields was first described by Paulus, H. and Kennedy, E.P., *J. Biol. Chem.* 235, 1303 (1960), and later by Agranoff and Suomi, *Biochem. Prep.* 10, 47–51 (1963). The latter scientists condensed cytidine-5'-monophosphate-morpholidate (CMP-morpholidate) with DL-phosphatidic acid (DL-diacylglycerol phosphate) in anhydrous pyridine to form CDP-DG. Essentially the same synthesis was generally followed in the art for the preparation of various CDP-DG analogs. However, this synthesis route involves long reaction times and a troublesome purification procedure, due to the presence of unreacted phosphatidic acid, resulting in low yields of pure product. The synthesis reported by Agranoff and Suomi took over 65 hours, and the yield of 70% pure CDP-DL-dipalmitin was described to be between 30 and 60%. According to a footnote on page 50 of the Agranoff and Suomi article, using L-phosphatidic acid, the reviewers obtained an overall yield of 32% of a product having a purity of 89%. Later authors, following the Agranoff-Suomi synthesis, typically reported 20 to 30% yields for the end product [see e.g. Carman and Fischl, *J. Food Biochem.* 4, 53–59 (1980)].

Furthermore, when performing the Agranoff and Suomi synthesis, a frozen mixture of the reactants in benzene is first lyophilized, and when the benzene has been completely removed, anhydrous pyridine is introduced. The success of the reaction appears to be related to the solubility of the reactants in pyridine after they are lyophilized out of benzene. If the lyophilization is performed correctly, a fluffy white material is formed which easily dissolves in pyridine. However, the lyophilization step is often unsuccessful, and as a result, the reaction does not take place. These problems have been addressed by Carman and Fischl, *Supra*, who modified the Agranoff-Suomi method by performing the reaction in chloroform instead of pyridine, using 4-dimethylaminopyridine as a catalyst. This modification eliminated the lyophilization step, and resulted in yields of about 40% in about 48 hours.

The British Patent Application No. 2,168,350 (Hong) describes the preparation of new nucleoside conjugates derived from 1-O-alkyl-2-O-acylglycero-3-phosphates. The new compounds were predominantly prepared essentially following the Agranoff and Suomi method, and, in agreement with other art, about 30% yields were reported for the end product. Although the reaction of a corresponding phospholipid morpholidate with a corresponding nucleotide is also contemplated, according to the only illustrative example offered in the Hong application (Example 3, Method B), this reaction route apparently did not offer any advantage over the Agranoff and Suomi method. The reaction of racemic 1-O-hexadecyl-2-O-palmitoylglycero-3-phosphate morpholidate with ara-CMP was allowed to proceed for seven days, and the yield of the desired racemic 1-O-hexadecyl-2-O-palmitoylglycero-3-phosphate was reported to be 30%.

The fact that Hong did not attribute any particular advantage to reacting a phosphatidic acid morpholidate with a suitable nucleoside over the traditional approach of reacting a nucleoside-5'-monophosphate morpholidate with a phosphatidic acid derivative is supported by his later work. For example, according to Hong et al., *J. Med. Chem.* 33, 1380–1386 (1990) 1-β-D-arabinofuranosylcytosine and cytidine conjugates of thioether lipids were prepared from 1-S-alkylphosphatidic acid derivatives and the corresponding nucleoside morpholidates, and 15–38% overall yields were reported.

SUMMARY OF THE INVENTION

We have surprisingly found that if the synthesis known in the art for the preparation of nucleoside diphosphate diglycerides is modified such that instead of reacting a nucleoside-5'-monophosphate morpholidate with a phosphatidic acid derivative, first the phosphatidic acid derivative is converted into a corresponding amidate, for example morpholidate, which is then reacted with the free acid or salt form of the desired nucleoside-5'-monophosphate, the yields are substantially increased, and the reaction time is significantly shorter. Instead of amidates, other phosphatidic acid derivatives in which one of the phosphate hydroxyls is replaced by a leaving group, may also be employed with similar results.

For example, when nucleoside diphosphate diglycerides were synthesized by the improved methods of the present invention, the reaction time was reduced from several days to 3 to 10 hours, and the yield was increased to about 60 to 80%. Furthermore, the purification of the nucleoside diphosphate diglycerides is highly facilitated. When synthesizing the target compounds by the new route, phosphatidic acid is almost completely absent in the reaction mixture, which greatly simplifies and speeds up purification of the desired product. Crude reaction mixtures can easily be purified in a single HPLC procedure, resulting in faster elution, and higher yields of pure compound.

It has further been found that the improved results are not limited to nucleoside diphosphate diglyceride synthesis; the synthesis route according to the present invention is generally applicable to the preparation of monoglyceride diphosphate, diglyceride diphosphate and and corresponding triphosphate derivatives of various compounds, such as nucleosides, phosphonoformates, and nucleoside phosphonoformates and analogues thereof.

The invention therefore provides an improved process for coupling a monoglyceride or diglyceride monophosphate species to a compound having a terminal phosphate group by means of a pyrophosphate linkage. In one aspect, the present invention relates to an improved method for the synthesis of mono- or diglyceride di- or triphosphate derivatives wherein a phospholipid having the formula wherein $R^1$ and $R^2$ are independently hydroxyl or branched or unbranched aliphatic groups having from 1 to 24 carbon atoms and 0 to 6 sites of unsaturation; and L is a leaving group, is reacted with a compound having a terminal monophosphate or diphosphate group, in the presence of a basic catalyst, under anhydrous conditions, whereby a glyceride di- or triphosphate derivative is formed; provided that said phospholipid derivative is not a 1-O-alkyl-2-O-acylglycero-3-phosphate morpholidate when said second compound is a nucleoside or nucleoside analogue comprising an adenine, cytosine, 5-fluorouracil, 5-azacytosine, 6-mercaptopurine, or 7-deazaadenine group attached to a pentose which is a ribose or arabinose.

The leaving group, L, is preferably an amine, which can be a morpholino or imidazole group; the process can be carried out at a temperature between about 4° C. and 80° C., preferably at room temperature; the preferred solvent for the coupling reaction is pyridine, and anhydrous pyridine is particularly preferred.

In another aspect, the present invention concerns a process for the preparation of a glyceride di- or triphosphate derivative of formula (II)

wherein

A is oxygen, sulfur, or methylene k is 0 or 1; and

Nu is a nucleoside, or a nucleoside analogue; and salts thereof, comprising:

reacting a phospholipid derivative of formula (I) as hereinabove defined, with a mono- or diphosphate having the formula wherein A, Nu, and k, are as hereinabove defined, in the presence of a basic catalyst, under anhydrous conditions, whereby a phospholipid nucleoside derivative is formed;

providing that when A is oxygen, and k is O, said phospholipid derivative is not a 1-O-alkyl-2-O-acylglycero-3-phosphate morpholidate when said second compound is a nucleoside or nucleoside analogue comprising an adenine, cytosine, 5-fluorouracil, 5-azacytosine, 6-mercaptopurine, or 7-deazaadenine group attached to a pentose which is a ribose or arabinose.

In the methods of the present invention, a molar ratio between the glyceride monophosphate species and nucleo- side reactants is between about 2:1 and about 1:2, preferably between 2:1 and 1:2, and most preferably about 1:1. The preferred basic catalyst is pyridine and the reaction is preferably performed in anhydrous pyridine as a solvent. The reaction time preferably does not exceed 10 hours. The reaction temperature preferably is between about 4° C. and about 80° C., most preferably room temperature.

The invention includes a further step of purifying the obtained nucleoside diphosphate diglyceride, performed, for example, by high pressure liquid chromatography, or on a DEAE Sephadex® column.

The process can be used in the preparation of naturally occurring complex lipid, for example, any glyceride derivatives of the naturally occurring ribose and 2'deoxyribose derivatives of adenine, guanine, cytosine and thymine, including the diphosphate diglycerides of cytosine (CDP diglyceride).

The process can be used in the preparation of glyceride derivatives of nucleoside analogues wherein either a purine or pyrimidine base or a sugar moiety is an analogue of a naturally occurring base or sugar. The process is particularly useful in the preparation of lipid derivatives of arabinose containing nucleosides, for example 1-(2'-deoxy-2'-fluoro-1-β-arabinosyl)-5-iodocytosine (FIAC); 1-(2'-deoxy-2'-fluoro-1-β-D-arabinofuranosyl)-5-iodouracil (FIAU), 1-(2'-deoxy-2'-fluoro-1-β-D-arabinofuranosyl)-5-methyluracil (FMAU); 1-(2'-deoxy-2'-fluoro-1-β-D-arabino-furanosyl)-5-ethyluracil (FEAU); 9-β-D-arabinofuranosyl-adenine (ara-A); or 1-β-D-arabinofuranosylcytosine (ara-C); acyclic nucleoside analogues, for example, 9-(2-hydroxy-ethoxymethyl)guanine (acyclovir, ACV).

The invention further provides an improved process for the preparation of a glyceride phosphate phosphonoacid derivative having the formula (IV)

wherein

D is a —(CH$_2$)$_m$—C(O)O- group;

m is 0 or 1;

k is 0 or 1;

Nu is a nucleoside or a nucleoside analogue; and n is 0 or 1 and salts thereof, comprising: reacting a glyceride monophosphate derivative of formula (I) as hereinabove defined with a phosphonoacid having the formula (V)

or to the phosphonoacid linked by carboxyester to a nucleoside or nucleoside analogue and having the formula (Va)

wherein D, k, Nu and m are as hereinabove defined, in the presence of a basic catalyst, under anhydrous conditions.

In a preferred embodiments of the invention, at least one of $R^1$ and $R^2$ has the structure CH$_3$—(CH$_2$)$_a$—(CH=CH—CH$_2$)$_b$—(CH$_2$)$_c$—Y—, wherein the sum of a, b and c is from 1 to 23, b is 0 to 6, and Y is —C(O)O—, —CH$_2$—O—, —CH=CH—O—, —C(O)S—, —CH$_2$—S—, or —CH=CH—S—.

According to a further preferred embodiment of the process according to the present invention, compounds which are diglyceride mono- or diphosphates of nucleosides or nucleoside analogues, or diglycerides of phosphonoacids, phosphononucleosides, or phosphononucleoside analogues, comprise at least one of $R^1$ and $R^2$ having the formula CH$_3$(CH$_2$)$_a$—C(O)O—wherein a is an integer from 10 to 16.

Following the synthesis of the present invention, the glyceride diphosphate or triphosphate derivatives can be obtained in the form of their salts, for example metal salts. The preparation of such salts is also within the scope of the present invention.

In all of the above processes, the leaving group in the starting phospholipid derivative preferably is an amino group, most preferably a cyclic amino group, such as a morpholino group or an imidazole group.

In a further aspect, the present invention relates to the new phospholipid derivatives of the formula (I)

(I)

wherein $R^1$ and $R^2$ are independently hydroxyl or an aliphatic group having the structure CH$_3$—(CH$_2$)$_a$—(CH=CH—CH$_2$)$_b$—(CH$_2$)$_c$—Y—wherein the sum of a, b and c is from 1 to 23, b is 0 to 6, and Y is —C(O)O—, —CH$_2$—O—, —CH=CH—O—, —C(O)S—, —CH$_2$—S—, or —CH=CH—S—, and L is an amino group. Morpholine is a preferred amino group.

Preferred glyceride monophosphate derivatives are 1,2-dilauroyl-sn-glycero-3-phosphoro-morpholidate; 1,2-dimyristoyl-sn-glycero-3-phosphoro-morpholidate; 1,2-dipalmitoyl-sn-glycero-3-phosphoro-morpholidate; 1,2-dioleoyl-sn-glycero-3-phosphoro-morpholidate; and 1-O-hexadecyl-sn-glycero-3-phosphoro-morpholidate.

In a still further embodiment, the present invention relates to a process for the preparation of the new intermediates of formula (I), wherein the substituents are as defined above, by reacting a phospholipid of formula (VI)

(VI)

wherein the substituents have the same meaning as defined above, or a salt thereof, with a corresponding amine, whereby a phospholipid derivative of formula I is produced.

BRIEF DESCRIPTION OF FIGURES

Lane 1: Method A after 5 hours.

Lane 2: Method A after 10 hours.

Lane 3: Method B after 10 hours.

Lane 4: Method B after 5 days. The AZT-DP-DMG product is indicated by arrows. Note the large amount of remaining PA in Method B (lanes 3 and 4 in plate A, below the product).

A=3dT-DP-DMG

B=unknown product; Pi positive (strong)

C=unknown product; U.V. positive, Pi positive (weak)

D=DMPA morpholidate

E=3dTMP.

DETAILED DESCRIPTION OF THE INVENTION

1. Definitions

The term "nucleoside" as used throughout the specification and claims includes naturally occurring nucleosides and their analogues. The naturally occurring nucleoside are those nucleoside species comprising a pyrimidine or purine base e.g., adenine, guanine, cytosine, uracil, inosine, or thymine, linked to a ribose (ribonucleoside) or 2'-deoxyribose (deoxyribonucleoside) 5-carbon cyclic sugar group. Ribonucleosides and deoxynucleosides are phosphorylated at the 5'site and enzymatically assembled into RNA and DNA respectively in vivo.

Nucleoside analogues may comprise a naturally occurring purine or pyrimidine base attached to an analogue of the naturally occurring ribose group, an analogue of a purine or pyrimidine base attached to a ribose or 2'-deoxyribose group which is present in naturally occurring nucleosides, or alternatively, both the base and the ribose moieties of the nucleoside analogues may be different from the moieties found in nature. A nucleoside analogue may also comprise either a naturally occurring base or a base analogue attached to a nonribose sugar moiety. Analogs of both the purine or pyrimidine base and the ribose group can differ from a corresponding naturally occurring moiety by having new substituent groups attached thereto, by having naturally occurring substituent groups deleted therefrom, or by having atoms normally present replaced by others.

Naturally occurring nucleosides have a purine or pyrimidine base attached to ribose or a ribose residue through the nitrogen in the 9 position of the purines and through the nitrogen in the 1 position of the pyrimidines. These nitrogens are linked by a β-N-glycosyl linkage to the 1'carbon of the pentose residue. Nucleoside analogues may comprise a purine or pyrimidine base attached to the pentose moiety in a non-naturally occurring linkage such as, for example, through the nitrogen at the 3 position rather than the 1 position of pyrimidine.

Nucleoside analogues are believed to have cytotoxic or antiviral effects because they inhibit DNA or RNA synthesis in the proliferation of tumor cells or in the process of viral replication.

Specific classes of nucleoside analogues found to have these effects are as follows:

Dideoxynucleosides wherein the hydroxyl groups at both the 2' and 3'-position of ribose are replaced by hydrogen, for example, 2', 3'-dideoxycytidine (ddc); 2', 3'-dideoxyinosine (ddI); 2', 3'-dideoxyadenosine (ddA); 3'-deoxythymidine (3dT); and 2', 3'-dideoxyguanosine (ddG);. When a dideoxynucleoside is incorporated into a growing DNA chain, the absence of the 3'-hydroxyl on its ribose group makes it impossible to attach another nucleoside and the chain is terminated. Dideoxynucleosides are particularly useful in treating retroviral infections such as AIDS, hairy cell leukemia, topical spastic paraparesis and hepatitis B, where viral replication requires the transcription of viral RNA into DNA by viral reverse transcriptase.

Acyclic nucleosides wherein the acyclic pentose residue is a fragment of a cyclic pentose, such as an hydroxylated 2-propoxymethyl residue or an hydroxylated ethoxymethyl residue. Particular nucleoside residues having these structures include 2-amino-1,9-dihydro-9-|(2-hydroxy-ethoxy)methyl|-6H-purine-6-one (acyclovir) or ganciclovir (DHPG), pencyclovir and famcyclovir. While the phosphate groups are generally connected to the 5' carbon of the pentoses in the nucleoside monophosphate reactants in the methods of the present invention, it is important to recognize that in analogues having pentose residues that are not complete pentoses, the phosphate groups are connected to the carbon that would have been the 5' carbon if the pentose were complete. In these pentose fragments, the 2' and/or 3' carbons may be missing; nevertheless, they are considered to be nucleoside derivatives within the meaning of present invention, and the carbon atom to which the phosphate groups are connected will be referred to herein as the 5' carbon for purposes of consistency of usage.

3'-azido-2', 3'-dideoxypyrimidine nucleosides wherein the 3'-hydroxyl of the nucleoside pentose is replaced by $N_3$, for example AZT, AZT-P-AZT, AZT-P-dda, AZT-P-ddi, AzddClU, AzddMeC, AzddMeC N4-OH, AzddMeC N4Me, AZT-P-CyE-dda, AzddEtU(CS-85), AzddU(CS-87), AzddC (CS-91), AzddFC, AzddBrU, and AzddIU.

Arabinose-containing nucleosides wherein the naturally-occurring pentose moiety of the nucleoside, ribose, is replaced by its 2'-epimer, arabinose, which may be in furanose form, for example: 1-(2'-deoxy-2'-fluoro-1-β- arabinosyl)-5-iodocytosine(FIAC); 1-(2'-deoxy-2'-fluoro-1-β-D-arabinofuranosyl)-5-iodouracil (FIAU); 1-(2'-deoxy-2'-fluoro-1-β-D-arabinofuranosyl)-5-methyluracil (FMAU); 1-(2'-deoxy-2'-fluoro-1-β-D-arabinofuranosyl)-5-ethyluracil (FEAU); 9-β-D-arabinofuranosyladenine (ara-A); 9-β-D-arabinofuranosylguanine (ara-G); 1-β-D-arabinofuranosylridine (ara-U); 1-β-D-arabinofuranosylthymine (ara-T);and 1-β-D-arabinofuranosylcytidine (ara-C). 3'-halopyrimidine dideoxynucleosides wherein the 3'-hydroxyl of the nucleoside pentose is replaced by a halogen, usually fluorine, for example 3'-fluoro-5-methyldeoxycytidine (FddMeCyt), 3'-chloro-5-methyldeoxycytidine (ClddMeCyt), 3-FddClU, 3-FddU, 3-FddT, 3-FddBrU, and 3-FddEtU.

2', 3'-didehydro-2', 3'-dideoxynucleosides (D4 nucleosides) for example, 2', 3'-didehydro-2', 3'-dideoxythymidine (ddeThd or D4T), D4C, D4MeC, and D4A.

Other nucleoside analogues may comprise more than one analogous feature, for example, 5-F-ddC; 2', 3'-dideoxy-3'-fluorothymidine (FddThd); 3'-fluoro-5-methyldeoxycytidine (FddMeCyt); 3-chloro-5-methyldeoxycytidine (ClddMeCyt); 3'-amino-5-methyldeoxycytidine (AddMeCyt); ddDAPR(diaminopurine); ddMeA(N6 methyl); and the class comprising sugar-substituted dideoxypurine nucleosides, for example, 3-N$_3$ddDAPR, 3-N$_3$ddG, 3-FddDAPR, 3-FddG, 3-FddaraA, and 3-FddA.

Antimetabolite and cytotoxic agents 6-mercaptopurine-2'-deoxyriboside, 1,7-dihydro-6H-purine-6thione (Purinethol, Burroughs-Wellcome, Research Triangle Park, N.C. 27709); thioguanine, 2-amino-1,7-dihydro-6H-purine-6-thione-2'-deoxyriboside (Tabloid®, Burroughs-Wellcome); FUDR, 2'-deoxy-5-fluorouridine (Floxuridine®, Roche Laboratories, Nutley, N.J. 07110).

Preferred nucleoside analogues for use in preparing lipid derivatives according to the invention are those used in the treatment of AIDS, including 3'-azido, 3'-deoxythymidine (azidothymidine or AZT); 3'-deoxythymidine (3dT); 2',3'-dideoxycytidine (ddC); 2', 3'-dideoxyadenosine (ddA); and 2', 3'-dideoxyguanosine (ddG). AZT, 3dT, ddC, and ddG are most preferred analogues at present.

The didehydropyrimidines, as well as carbovir, a carbocyclic 2', 3'-didehydroguanosine, are also preferred. The 3'-azido derivatives of deoxyguanosine (AZG) and the pyrimidine, deoxyuridine, and the 3'-fluoro derivatives of deoxythymidine and deoxyguanosine are preferred as well. Among the 2',6'-diaminopurines, the 2', 3'-deoxyriboside and its 3'-fluoro and 3'-azido derivatives are preferred. Among the acyclic sugar derivatives, 9-(4,-hydroxy-1',2'-butadienyl)adenine (adenallene) and its cytosine equivalent are preferred. Preferred acyclic derivatives having a purine or diaminopurine base are 9-(2-phosphonylmethoxyethyl) adenine and phosphonomethoxyethyl deoxydiaminopurine (PMEDADP).

Stereoisomers of these nucleosides, such as 2'-fluoro-ara-ddA, may be advantageous because of their resistance to acid-catalyzed hydrolysis of the glycosidic bond, which prolongs their antiviral activity. In such cases, they are preferred.

Diglyceride diphosphate derivatives of nucleoside analogues having an antiviral effect have been found to be more effective than the nucleoside analogue alone in the treatment of herpes, cytomegalovirus and hepatitis B infections. Accordingly, one may utilize the lipid derivatives of acyclovir, ganciclovir, 1-(2'-deoxy-2'-fluoro-1-β-D-arabinofuranosyl)-5-iodocytosine (FIAC), 1(2'-deoxy-2'-fluoro-1-β-D-arabinofuranosyl)-5-iodouracil (FIAU), 1-(2'deoxy-2'-fluoro-1-β-D-arabinofuranosyl)-5-methyluracil (FMAU), or 1-(2'-deoxy-2'-fluoro-1-β-D-arabinofuranosyl)-5-ethyluracil (FEAU) in appropriate therapies for these infections.

All these and similar nucleoside analogs, and particularly the antiviral nucleoside analogs disclosed in the co-pending patent applications U.S. Ser. No. 373,088, filed Jun. 28, 1989, now U.S. Pat. No. 5,223,263, and U.S. Ser. No. 440,898, filed Nov. 22, 1989, which now U.S. Pat. No. 5,194,654 are incorporated by reference, are encompassed by the term "nucleoside" as used in connection with the present invention.

Among the phospholipids described herein, the terms "glycerol monophosphate derivative", "glycerol diphosphate derivative" and "glycerol triphosphate derivative" and their grammatical variants, as used throughout the specification and claims refer to glycerol derivatives in which one of the glycerol hydroxyls of the structure is replaced by a moiety comprising one, two or three phosphate groups. "Glyceride" include lipid moieties wherein one or both of the glyceryl hydroxyls of the glycerol phosphate derivatives are replaced by an aliphatic group, as defined below.

Preferred are the glycerol mono-, di- and triphosphate derivatives in which one or both glyceryl hydroxyls that are not replaced by a mono-, di- or triphosphate group are replaced by aliphatic hydrocarbon chains linked to the glyceryl moiety by ester or ether linkages.

The term "phosphatidic acid" is most often used to describe phospholipids in which two hydroxyl groups of the glycerol moiety are esterified by $C_{1-24}$ aliphatic groups and the third one by a phosphate group. As used throughout the specification and claims, this term includes naturally occurring phosphatidic acids, synthetic phosphatidic acid species, and synthetic analogs of phosphatidic acid, including racemic, sn-glycerol-1-phosphate and sn-glycerol-3-phosphate. Naturally occurring phosphatidic acid can be readily obtained by cleavage of plant or animal phosphoglycerides, such as phosphatidylcholine, with phospholipase D [Kates, M. and Sastry, C. S., *Methods in Enzymology* 14, 197–203 (1969)], and can, for example, be isolated from egg lecithin by methods known in the art. The naturally occurring phosphatidic acid is not a single molecular species, rather is a mixture of various diacylglycerol phosphates. The term "phosphatidic acid" is also used to include lyso species, having only one glyceryl hydroxyl replaced by an aliphatic group. It also include those species having one or both glyceryl hydroxyls replaced by aliphatic groups in ether, rather than ester linkage. Phosphatidic acids and their synthetic analogs may, for example, be synthesized as described by Lapidot et al., *Chem. Phys. Lipids* 3, 125 (1969) (acylation of glycero-3-phosphate) and Eibl, H. and Blume, A., *Biochim. Biophys. Acta* 553, 476 (1979) (phosphorylation of 1,2-diacylglycerol or ether analogs).

The term "aliphatic group" is used in the broadest sense to describe non-aromatic groups and is not limited to aliphatic groups containing only hydrogen and carbon. Aliphatic groups including one or more heteroatoms, such as oxygen or sulfur are also within this definition. Accordingly, the definition covers ester, thioester, ether or thioether groups attached to an aliphatic hydrocarbon moiety.

A preferred group of phosphatidic acids can be encompassed by the following formula (A)

(A)

wherein $R^1$ and $R^2$ may be the same or different, and are aliphatic hydrocarbon groups having from 1 to 24 carbon atoms, and 0 to 6 sites of unsaturation. The aliphatic hydrocarbon groups represented by $R^1$ and $R^2$ preferably have the structure $CH_3—(CH_2)_a—(CH=CH—CH_2)_b—(CH_2)_c$-, wherein the sum of a, b and c is from 1 to 23; and b is 0 to 6. These aliphatic groups in acyl ester linkage as shown in formula (A), comprise naturally occurring saturated fatty acids, such as lauric, myristic, palmitic, stearic, arachidic and lignoceric acids, and naturally occurring unsaturated fatty acids, such as palmitoleic, oleic, linoleic, linolenic and arachidonic acids. In other embodiments, the aliphatic groups $R^1$ and $R^2$ can be branched chains of the same carbon atom number, and comprise primary or secondary alkanol or alkoxy groups, cyclopropane groups, and internal ether linkages.

The term "leaving group" is used to refer to any group that is readily removed from the phosphate moiety of the phospholipid derivative (e.g. phosphatidic acid) it is attached to, under the conditions of the condensation reaction with a corresponding compound containing a terminal phosphate group, for example a nucleoside-5'-monophosphate (either in free acid or in salt form). Since in the synthesis of the present invention amidates are prefereably used, the leaving group preferably is an amino group. However, other leaving groups, such as diphenylphosphate [Heinz et al., *Eur. J. Biochem.* 184, 445 (1989)], or diphenyl pyrophosphate are also suitable.

The term "amino group" is used in a broad sense and includes primary, secondary and tertiary amines, for example, aliphatic amines, such as diisopropylamine, triethylamine, tributylamine (mono-, di- or tri-$C_{1-10}$-alkyl) amines, or aromatic amines, such as diphenylamine, benzidine or toluidines, or heterocyclic amines, such as pyridine, picolines, pyrrole, pyrazole, quinoline, carbazole or quinaldine, in which the nitrogen atom of the amino group is part of a heterocyclic ring. In fact, the preferred phosphatidic acid amidate is phosphatidic acid morpholidate, wherein the "amino group" is a morpholino group. Other suitable amidates include, but are not limited to, imidazolidate, anisidate, piperidate and 1,1'-carbonyldiimidazole. The phospholipid amidates of the present invention (Formula I) are new compounds, and can be prepared by reacting a corresponding phospholipid, in free acid or salt form, with a suitable amine. The preparation of phosphatidic acid morpholidate is illustrated in the Examples hereinafter.

The basic catalyst used in the process of the present invention serves to convert the hydroxyl of the phosphate group to $O^{31}$, and may, for example, be pyridine or 4'-dimethylaminopyridine.

2. Description of Preferred Embodiments

According to a preferred embodiment of the present invention, nucleoside diphosphate or triphosphate diglycerides are prepared by reacting corresponding phosphatidic acid morpholidates with nucleoside-5'-monophosphates or -5'-diphosphates in anhydrous pyridine. The phosphatidic acid morpholidates may be prepared and further reacted in a salt form, for example in the form of 4'-morpholine-N,N'-dicyclohexylcarboxamidinium salt, as shown hereinbelow, in the Example. Similarly, the target nucleoside di- or triphosphate diglycerides can be obtained in the form of their salts, for example, as metal salts, by means of treatment with a base, preferably an inorganic base, as known to those in the art.

Phosphatidic acid morpholidates may be prepared from "free" phosphatidic acids and morpholine, preferably in a solvent mixture of chloroform and tert-butanol. The resultant phosphatidic acid morpholidate is lyophilized.

Thereafter, the lyophilized morpholidate and the corresponding nucleoside-5'-monophosphate are dissolved in anhydrous pyridine, and the reaction is allowed to proceed at room temperature. The molar ratio of phosphatidic acid morpholidate and nucleoside-5'-monophosphate typically is between about 2:1 and 1:2, preferably between about 2:1 and 1:1. The progress of the reaction can be monitored by thin layer chromatography (TLC). The speed of the reaction varies depending on the actual reactants. In some instances optimum conversions is reached in less than an hour. Generally, the reaction is complete within about 5 to 10 hours. The yields typically are between about 60% and about 80%.

The obtained nucleoside di- and triphosphate diglycerides are essentially free of phosphatidic acid, which highly simplifies and speeds up their purification. Crude reaction mixtures can easily be purified in a single HPLC procedure, resulting in larger amounts of pure product and faster elution.

Alternatively, phosphatidic acid morpholidates may also be synthesized directly from the disodium salt of phosphatidic acid, without prior conversion to the free acid form. This is done under the same reaction conditions as hereinabove described, except that small amounts of methanol/water (1:1 v/v) are usually added to obtain a clear solution. The yields obtained by this variant of the process do not differ significantly from the yields obtained when using free phosphatidic acid as a starting compound. Also, the morpholidate prepared this way reacts equally well with the 35 corresponding nucleoside-5'-mono- or diphosphate.

A preferred group of the nucleoside diphosphate diglycerides that can be prepared in accordance with the method of the present invention is encompassed by the following formula (II)

(II)

where in $R_1$ and $R_2$ independently are hydroxyl or aliphatic groups having from 1 to 24 carbon atoms, and 0 to 6 sites of unsaturation;

A is oxygen, sulfur, or methylene, k is 0 or 1;

n is 0 or 1; and

Nu is a nucleoside or nucleoside analogue.

The method of the invention can be used to prepare glycerol, monoglyceride and diglyceride derivatives of naturally occurring nucleosides, for example, adenine diphosphate, and to prepare the naturally occurring intermediate of lipid metabolism, cytidine diphosphate diglyceride.

The methods are also useful in preparing diglyceride diphosphate derivatives of cytotoxic and antiviral nucleoside analogues. Particularly preferred are within this group: (3'-azido-3'-deoxy)thymidine-5'-diphosphate-(1,2-dilauroyl)glycerol (AZT-DP-DLG); (3'-azido-3'-deoxy) thymidine-5'-diphosphate-(1,2-dimyristoyl) glycerol (AZT-DP-DMG); (3'-deoxy) thymidine-5'-diphosphate-(1,2-dilauroyl)glycerol (3dT-DP-DLG); (3'-deoxy) thymidine-5'-diphosphate-(1,2-dimyristoyl)glycerol (3dT-DP-DMG); (2',3'-dideoxy) cytidine-5'-diphosphate-(1,2-dilauroyl)glycerol (ddC-DP-DLG); (2', 3'-dideoxy) cytidine-5'-diphosphate-(1,2-dimyristoyl)glycerol (ddC-DP-DMG); acyclovir-diphosphate-(1,2-dipalmitoyl)glycerol; acyclovir-diphosphate-(1,2-dimyristoyl)glycerol; acyclovir-diphosphate-(1-O-hexadecyl)glycerol; 1,2-dilauroylglycero-3-phosphate-(pyro)-phosphonoformate; 1,2-dimyristoylglycero-3-phosphate-(pyro)-phosphonoformate; 1-(2'-deoxy-2-fluoro-β-D-arabinofuranosyl)-5-iodouracil-5'-diphosphate-L-(1,2-dipalmitoyl)glycerol (FIAU-DP-DPG).

According to another preferred embodiment of the present invention, diacylglycerol phosphate phosphonoacids are synthesized by preparing the morpholidate of the corresponding phosphatidic acid, and coupling to the corresponding phosphonoacid, which can be phosphonoformate or phosphonoacetate. In another preferred embodiment, the new synthesis is adapted for the preparation of diacylglycerol phosphate phosphonoacids to which nucleosides including those having a cytotoxic or antiviralactivity are coupled, for example, by a carboxyl ester linkage. These classes of compounds have antiviral properties, and are disclosed in the co-pending application U.S. Ser. No. 440,898 (filed Nov. 22, 1989) now U.S. Pat. No. 5,194,654. Preferred phosphonoacid derivatives are 1,2-dilauroylglycero-3-phosphate-(pyro)-phosphonoformate; or 1,2-dimyristoylglycero-3-phosphate-(pyro)-phosphonoformate.

The chemical reactions described above are generally disclosed in terms of their broadest application to the methods of the invention. Occasionally, the reactions may not be applicable as described to the synthesis of each compound suggested within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, or by routine modification of reaction conditions. In all preparative methods, all starting materials are known or readily preparable from known starting materials.

It is believed that one skilled in the art can, using the preceding description, utilize the invention to its fullest extent. The following preferred embodiments are, therefore, to be construed as merely illustrative, and not limitative or the remainder of the disclosure in any way whatsoever.

EXAMPLE 1

Preparation of Nucleoside Diphosphate Diglycerides

A. Materials and Methods:

Dilauroyl and dimyristoyl phosphatidic acids, disodium salts were obtained from Avanti Polar lipids (Pelham, Ala., USA).

Dowex 50 W (50×2-200,100-200 mesh) 2',3'-dideoxycytidine, and 3'-deoxythymidine were products from Sigma Chemical Co. (St. Louis, Mo., USA); 3'-azido-3'-deoxythymidine and 3'-azido-3'-deoxythymidine-5'-monophosphate were obtained from Burroughs-Wellcome, Research Triangle Park, N.C. 27709). Morpholine, dicyclohexylcarbodiimide (DCC) and tertiary butyl alcohol (2-methyl-2-propanol, tBuOH) were the highest grade available from Aldrich Chemical Co. (Milwaukee, Wis.).

Phosphorus oxychloride, trimethylphosphate, silica 60 F 254 HPTLC plates (10×20 cm), silica 60 F254 aluminum plates (5×10 cm), HPLC grade solvents (Lichrosolv) and all other chemicals were from Merck (Darmstadt, FRG), unless stated otherwise.

Figure 2:
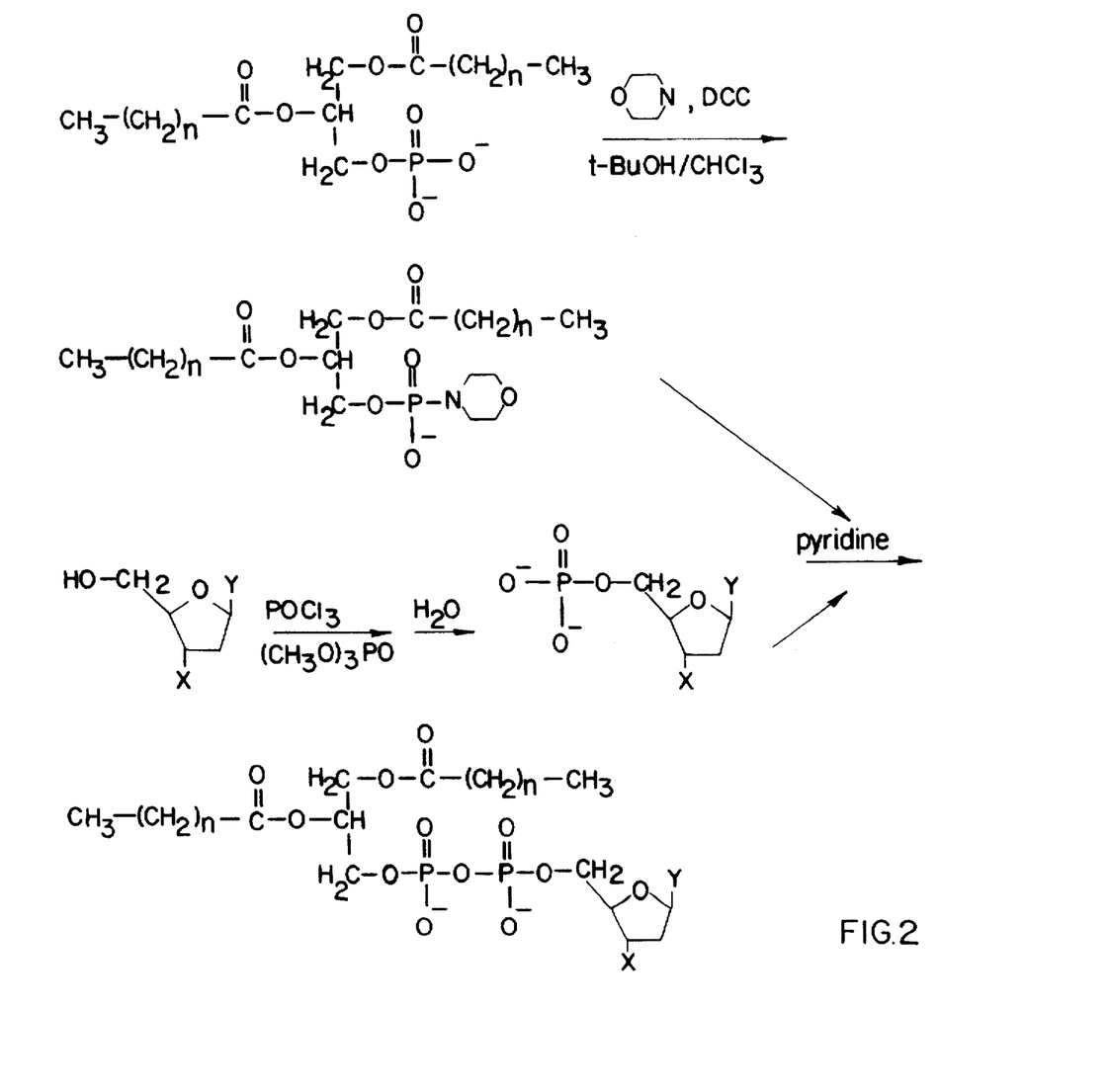
FIG. 2 illustrates a preferred embodiment of the chemical synthesis of nucleoside diphosphate diglycerides according to the present invention. The symbols X, Y and n are as defined in the legend.

Initially, the synthesis of deoxynucleoside-diphosphatediglycerides was done essentially following the procedure reported by Agranoff and Suomi, *Biochem. Prep.* 10, 46–51 (1963). Analysis and characterization of the purified compounds was done by UV/Pi ratios, IR- and $^1$H-NMR spectra. FIG. 2 shows the overall reaction scheme for the newly developed synthesis of the compounds. This procedure will be described in more detail below.

B. Phosphorylation of Nucleosides:

The phosphorylation of unprotected nucleosides with $POCl_3$ in $(CH_3O)_3PO$ was essentially performed as described by Yoshikawa, et al., *Tetrahedron Lett.* 50, 5065–5068 (1967); and Yoshikawa, M., Kato, et al., *Bull. Chem. Soc. Japan* 42, 3205–3208 (1967). To a cooled solution (0° C.) of 2 mmol $POCl_3$ in 3–4 ml $(CH_3O)_3PO$ the nucleoside (1 mmol) was added stepwise with stirring, the reaction temperature being held constant between 0° and 5° C. The progress of the reactions was monitored by means of HPLC using a Mono Q HR 5/5 anion exchange column (Pharmacia, Uppsala, Sweden). Typically 5 μl of the reaction mixture was neutralized with aqueous sodium hydroxide (final pH 7), and injected on the column. Elution was performed as follows: washing with water, elution with 0.1 M $NH_4HCO_3$ which elutes the nucleoside-5'-monophosphate, followed by a linear gradient of 0.1–0.6 M $NH_4HCO_3$, which elutes some higher phosphorylated products. The reaction was mostly completed within 45 to 75 minutes as judged by this method, and the reaction product was hydrolyzed and neutralized with 2 volumes of aqueous sodium hydroxide to a final pH of 7. Purification was as described above for the analysis of the reaction mixture. By this method, 10–20 mg of nucleoside-5'-monophosphate could be purified. Larger amounts were purified on a Sepharose Q fast flow column using the same elution conditions.

Yields varied between 80 and 96% after repeated lyophilization from water. TLC analysis (Silica 60/F254 plates, Merck) showed a single U.V. and Pi positive spot, using the developing system 1-propanol/25% $NH_3/H_2O$ (20:20:3 by volume):3'-azido-3'-deoxythymidine-5'-monophosphate $R_f$=0.63; 3'-deoxythymidine-5'-monophosphate Rf=0.61 and 2',3'dideoxycytidine-5'-monophosphate Rf=0.51.

C. Conversion of Phosphatidic Acid Salts To The Free-Acid Form:

Phosphatidic acids, di-sodium salts, were acidified by application of an extraction procedure according to Bligh and Dyer, *Can. J. Biochem.* 37, 911–917 (1959). Thus, 1 mmol of lipid was dissolved in a homogenous mixture of 100 ml $CHCl_3$, 200 ml MeOH, 100 ml 0.1 M HCl and stirred at room temperature for one hour. Then 100 ml $H_2O$ and 100 ml $CHCl_3$ were added, the separated $CHCl_3$ layer was isolated and the aqueous phase was extracted twice with 200 ml $CHCl_3$. The combined $CHCl_3$ extracts were evaporated to dryness and lyophilized. Yield: 95–100% phosphatidate as the free acid.

D. Synthesis of 1,2-diacyl-sn-glycero-3-phosphoromorpholidate (phosphatidic acid morpholidate):

Method A: From free phosphatidic acid: Free phosphatidic acid (1 mmol) was dissolved in 20 ml $CHCl_3$ and this solution was transferred to a two-necked round bottom flask, which contains 20 ml t-BuOH, 4 mmol morpholine and 4 mmol $H_{2O}$. This mixture was gently refluxed and a solution of 4 mmol DCC in 20 ml t-BuOH was added stepwise from a dropping funnel within 2 hours. The reaction was monitored by thin-layer chromatography using silica 60 F254 HPTLC plates and $CHCl_3$/MeOH/25% $NH_3$/$H_2O$ (70:38:8:2 v/v) as developing system. The reaction was judged to be completed by the appearance of a major $P_i$-positive spot ($R_f$=0.9) and the disappearance of the $P_i$-positive spot of the phosphatidic acid at $R_f$=0.09. The reaction mixture was taken to dryness and suspended in 50 ml $H_2O$ and transferred to a dropping funnel. The suspension was extracted three times with diethylether, evaporated to dryness and lyophilized Yield 70–95% of 1,2-diacyl-sn-glycero-3-phosphoro-morpholidate as the 4'-morpholine-N,N'-dicyclohexylcarboxamidinium salt. This compound was used without further purification for the synthesis of the nucleoside-diphosphate-diglycerides.

Method B: From phosphatidic acid,disodium salt: This reaction was performed essentially as described above. Sometimes, however, the reaction mixture had to be clarified by the addition of a minimum amount of methanol/water (1:1, v/v). The aqueous phase was extracted with chloroform or diethylether, evaporated, lyophilized and used in the condensation reaction without further purification.

E. Synthesis of Nucleoside-Diphosphate-Diglycerides:

Lyophilized mixtures of phosphatidic acid morpholidates and nucleoside-5' monophosphates were dissolved in pyridine and evaporated to dryness, only letting $N_2$ into the apparatus. This procedure was repeated several times and then a final amount of pyridine was added to give a clear solution. About 50% of the pyridine was evaporated and the reaction vessel was removed from the apparatus ($N_2$-stream), tightly stoppered and the reaction was checked every 30 minutes by means of TLC using $CHCl_3$/MeOH/ 25% $NH_3$/$H_2O$ (70/38/8/2,v/v) as the developing system. The reaction was completed within 5–10 hours as judged by the appearance of a major UV and $P_i$-positive spot at $R_f$ values between 0.25 and 0.30, depending on the nucleoside.

Synthesis of AZT-DP-DMG (Compound 1)

The influence of the molar ratio of the reactants on the yield of reaction was studied, by condensing dimyristoylphosphatidic acid (DMPA) morpholidate and AZT-5'-monophosphate in a 2:1, a 1:1 and a 1:2 ratio on a 0.14 millimolar scale based on the morpholidate. Yields based on weighing after final purification (see below) and a molecular weight of 956 for AZT-DP-DMG (Compound 1) were 81%, 80% and about 60% of the theoretical yield.

The following Compounds 2–5 were obtained analogously and in the yields shown by selecting an appropriate PA morpholidate and a nucleoside monophosphate having the indicated substituents according to the structures given in FIG. 2, and reacting them in a 1:1 ratio:

Compound Yield (2) 3dT-diphosphate dilauroylglycerol: X=H; Y=thymine; n=10 57%

(3) 3dT-diphosphate dimyristoylglycerol: X=H; Y=thymine; n=12 37%.

(4) ddc-diphosphate dilauroylglycerol: X=H; Y=cytosine; n=10 52%

(5) ddc-diphosphate dimyristoylglycerol: X=H; Y=thymine; n=12 61%

AZT-DP-DMG has also been synthesized on a 50 μmolar scale in a 1:1 ratio of DMPA-morpholidate and AZT-5'-monophosphate with similar yields.

F. Purification of the Compounds:

The crude reaction products were purified without further processing. The lyophilized reaction mixtures were dissolved in elution solvent or, alternatively, in a 1:1 (v./v.) mixture of chloroform and methanol, and purified by means of HPLC, using a silica μ Porasil® column (Waters Associates Inc., Milford, Mass. USA: 19 mm (I.D.)×30 cm (length)) and the solvent system hexane/2-propanol/25% $NH_3$/$H_2O$ (43:57:3:7 v/v). |Geurts van Kessel, et al., Biochim. Biophys. Acta 486, 524–530 (1977)|. Detection was performed by UV absorption at 206 nm. By this method 50–100 mg of crude product could be purified in half an hour.

$R_f$ values with TLC using developing system $CHCl_3$/MeOH/25%$NH_3$/$H_2O$ 70/38/8/2, v/v): AZT-DP-DG=0, 30; 3dT-DP-DG=0.29 and ddC-DP-DG=0.25.

When the compounds were stored at -20° C., little decomposition was observed (<5%) over a period of 3 months.

G. Discussion:

The influence of the molar ratio of the reactants on the yield of the synthesis of AZT-DP-DMG was determined. It was found that a 2:1 and 1:1 ratio of DMPA-morpholidate/ AZT-5'-monophosphate gave rise to a comparable result and from then on the equimolar ratio was used routinely. This result was confirmed by the small-scale (50 μmoles) synthesis of these compounds.

Figure 3:
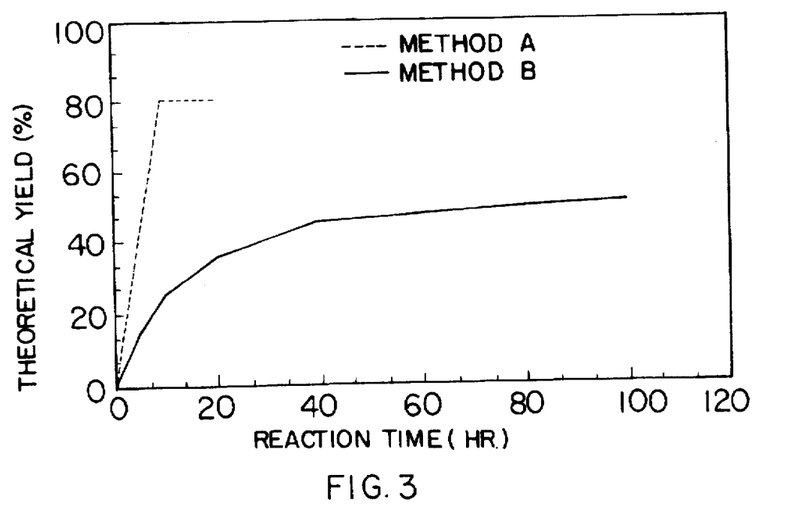
FIG. 3 is a comparison of the yields and reaction times of two different syntheses of AZT-5'-diphosphate-(1,2-dimyristoyl)glycerol (AZT-DP-DMG). Dashed line, Method A: present invention; solid line, Method B: conventional procedure (Agranoff and Suomi, *supra*). The figure clearly shows the advantage of Method A. The different yields were obtained quantitatively, based on $P_i$ and UV intensities with HPTLC. The final yields were determined after HPLC purification.

In FIG. 3 a comparison of the yields and reaction times of the synthesis of AZT-DP-DMG is made between the two condensation procedures for the preparation of nucleoside-diphosphate-diglycerides. Method A is the process according to the present invention, whereas Method B is the procedure that has been used widely in the literature, namely the condensation of phosphatidic acid and a nucleoside-5'-monophosphoromorpholidate (Agranoff et al., supra). The reactions were performed on scales varying from 0.05 to 0.5 mmolar, followed qualitatively by HPTLC and the yields quantified by weighing the product after purification by HPLC, as described.

The picture clearly shows two features that are highly in favor of synthesizing the compounds by Method A. Firstly, the reaction time is considerably reduced and secondly the yield of the reaction is increased to 60–80%.

The somewhat lower yields of the synthesis of compounds 2–5 is probably due to some residual ammonium-hydrogen carbonate, which is introduced during the purification procedure of the nucleoside-5'-monophosphates, a phenomenon which was also observed when using Method B. Thorough desalting of the purified nucleoside-phosphates will probably eliminate this effect.

Figure 4A:
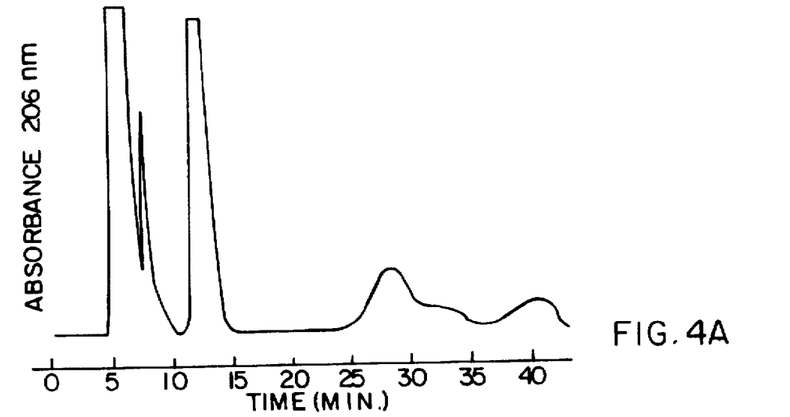
FIG. 4 shows the HPLC profiles of purifications of AZT-5'-diphosphate-(1,2-dimyristoyl)glycerol (AZT-DP-DMG) from crude reaction mixtures obtained by Methods A and B, respectively. Solvent: n-hexane/2-propanol/25%$NH_3$/$H_2O$ (43:57:3:7 v/v). Detection at 206 nm; flow: 14 ml/min. A: Method A; B: Method B. AZT-DP-DMG (eluted at 12 min.) is well separated from phosphatidic acid (PA) (eluted at 25–30 min.). During preparative HPLC the large amount of remaining PA in Method B partially overlaps with the product peak to cause lower yields of pure product.
Figure 4B:
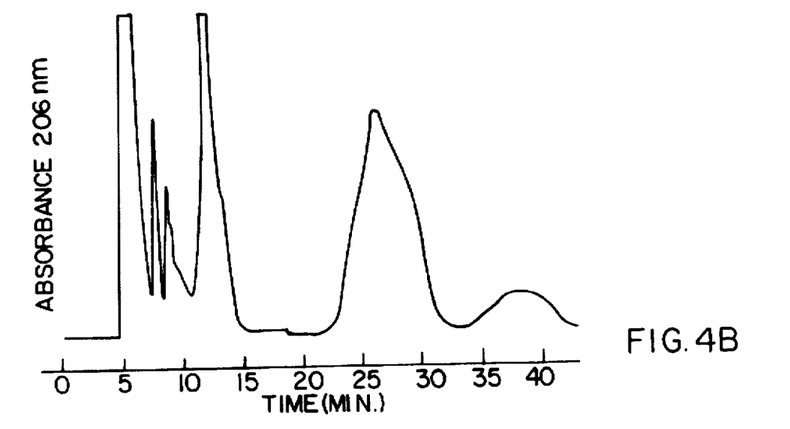
Figure 5:
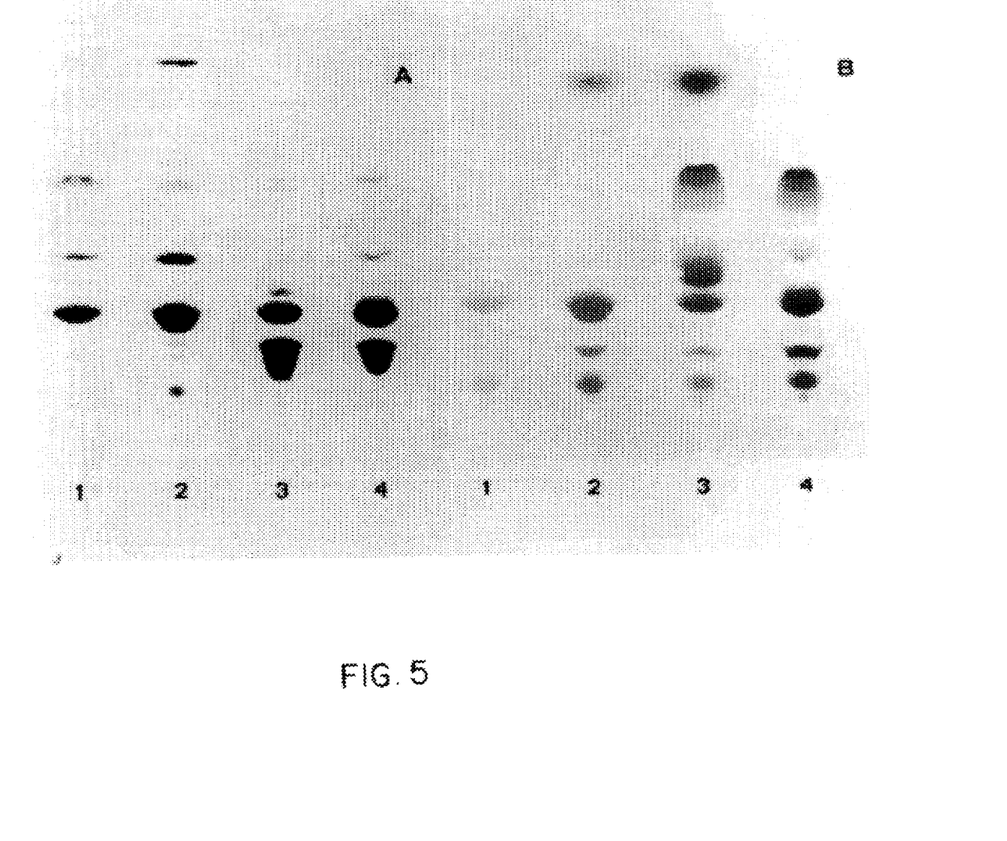
FIG. 5 shows the HPTLC pictures of the crude reaction mixtures obtained by the synthesis of AZT-DP-DMG according to Methods A and B, respectively. Plate A: stained with phosphorus reagent; Plate B: ultraviolet detection at 254 nm.

Considering the purification of the compounds, it was noted that this procedure is highly facilitated when the synthesis is performed by Method A. FIGS. 4A and 4B show pictures of HPLC purifications of compound 1, which were synthesized by Method A and B respectively. FIG. 5 shows HPTLC pictures of the reaction mixtures. Comparison of both HPTLC and HPLC profiles shows the almost complete absence of phosphatidic acid (FIG. 4A and FIG. 5A, lanes 1 and 2), or its abundant presence (FIG. 4B and FIG. 5A, lanes 3 and 4) in the respective reaction mixtures. Also the enrichment of the desired product in the reaction mixture of Method A when compared to that of Method B is clearly visualized both with respect to phosphate-containing and UV-positive compounds.

Throughout the literature on the synthesis of nucleoside-diphosphate-diglycerides, the purification of these compounds has been known to be difficult. See, for example, Agranoff, B.W. and Suomi, W. D., *Biochemical*

*Preparations*, 10:47–51 (1963); Prottey, C. and Hawthorne, J. W., *Biochem. J.*, 105:379–391 (1967); MacCoss, M. et al., *Biochem. Biophys. Res. Commun.*, 85 (2):714–723; Turcotte, J. et al., *Biochim. Biophys. Acta,* 619:604–618 (1980); and Ryu, E. K. et al., *J. Med. Chem.,* 25:1322–1329 (1982). These problems are mainly due to a considerable amount of residual phosphatidic acid in the reaction mixture. When synthesizing the compounds by the new route, however, phosphatidic acid is almost completely absent, and thus purification is simplified and speeded up.

In conclusion, we have synthesized some selected nucleoside-diphosphate-diglycerides with potential anti-retroviral activity by a new method, which is based on the condensation of a 1,2-diacyl-sn-glycero-3-phosphoromorpholidate and a nucleoside-5'-monophosphate. The method seems to be applicable generally for the synthesis of these compounds, independent of the nature of the nucleoside. The method has several advantages over the state of art procedure.

The yield of the reaction is improved (up to 60–80%) and reaction times are considerably reduced from several days to 5–10 hours (or even less). Another aspect, which is equally important, is the simplification of the purification procedure, because of the virtual absence of phosphatic acid in the reaction mixture. Because of this, crude reaction mixtures can easily be purified in a single HPLC procedure, giving larger amounts of pure product and faster elution.

EXAMPLE 2

Synthesis of

Acyclovir-Diphosphate(1,2Diacyl)Glycerols

The preparation of acyclovir derivatives according to the method of the invention presents particular difficulty because of the insolubility of acyclovir monophosphate. This difficulty is overcome by the following methods:

Method A: Acyclovir-Diphosphate(1,2-Dimyristoyl) Glycerol (ACV-DP-DMG):

One gram of sodium salt of dimyristoylphosphatidic acid (Avanti Polar Lipids, Birmingham, Ala.) was converted to free acid as described in Example 1, Part C. Dry dimyristoylphosphatidic acid was converted to the corresponding morpholidate as described in Example 1, Part D. 1.48 g of the lyophilized morpholidate compound and 0.610 g of dry acyclovir monophosphate were combined in 50 ml of dry pyridine, and evaporated to dryness under vacuum on a rotary evaporator. Finally, 50 ml of dry pyridine was added and concentrated to approximately 20 ml. To bring acyclovir monophosphate into solution required the addition of 10 ml of anhydrous dimethyl sulfoxide (DMSO) and heating the reaction vessel to 85° C. for 2 hours and at 45° C. for an additional 16 hours. Purified acyclovir-5'-diphosphate-(1,2-dimyristoyl)glycerol was isolated by HPLC as described in Example 1, eluting from the column at 18–20 minutes. The fractions were combined and lyophilized to yield a white powder. Alternatively, acyclovir diphosphate diglycerides may be purified by DEAE sephadex column chromatography as noted in Example 4 below. The compound was dissolved in chloroform/methanol (1:1 v/v) and spotted at the origin of a silica gel G plate and developed with chloroform/ methanol/concentrated ammonia (70:38:8 v/v). The product gave a U.V. and phosphorus positive spot with an Rf value of 0.23.

Method B: Acyclovir-Diphosphate(1,2-dipalmitoyl)glycerol (ACV-DP-DPG)

Dipalmitoyl phosphatidic acid morpholidate (DPPA morpholidate) was prepared as described in Example 1, using the sodium salt of phosphatidic acid directly for activation.

A: Preparation of Pyridine-soluble form of acyclovir monophosphate (ACVMP):

To a suspension of 80μmol ACVMP (as free acid) in 4 ml methanol, 160μmol tributylamine (TBA) or trioctylamine (TOA) was added, according to the procedure of Roseman, S. et al., *J. Amer. Chem. Soc.* 83:659–675 (1961). The mixture was vigorously stirred at room temperature and after 15 to 30 min a clear solution was obtained (occasionally additional base had to be added). After evaporation of methanol and lyophilization, the TBA- and TOA-salts of ACVMP were readily soluble in pyridine.

B: Synthesis of Acyclovir diphosphate diglyceride, dipalmitoyl (ACVDP-DPG):

To a solution of 40μmol ACVMP (as TBA- or TOA-salt) in anhydrous pyridine, 40 or 80μmol dimyristoyl phosphatidic acid morpholidate (DPPA morpholidate) in 2 ml anhydrous pyridine was added. After heating for 20 h at 60° C. in a waterbath, the reaction was stopped by evaporation of pyridine and extraction of the crude mixture using 0.1 N HCl as aqueous phase, according to Bligh, E. and Dyer, W., *Canad. J. Biochem.* 37:911–917 (1959).

C: Analysis of Reaction Mixture:

Aliquots of both the aqueous methanol and the chloroform layer were analyzed for ultraviolet absorbing materials by means of HPTLC (silica 60 F254 plates, 10×20 cm), using chloroform/methanol/25% ammonia/water (70:58:8:8), v/v) as the developing system. UV-positive spots were scraped from the plates, the silica was extracted with 2 ml chloroform/methanol/0.1N Hcl (1:2:1,v/v) and the amount of material in both phases was determined spectrophotometrically at 256 nm. The ratio A(256, aqueous) :A(256, chloroform) was at least 45:55. Since there was only one UV-positive spot in the chloroform layer, the yield of ACVDP-DG-DPG was about 55%.

D: Purification of ACVDP-DPG:

A crude reaction mixture containing ACVDP-DG-DPG, obtained by condensation of about 1.8 mmol ACVMP-TBA salt with 2.5 mmol DPPA morpholidate as described above, was extracted three times with chloroform according to Bligh, E. G. and Dyer, W. J. (*Can. J. Biochem.* 37:911–917 (1959)) and the combined chloroform layers were evaporated to dryness. The residue was dispersed in 15 ml chloroform/methanol/water (2:3:1, v/v), and this mixture was clarified upon heating for 30sec at 40° C. The solution was applied to a Q-Sepharose fast flow column (4.9 cm(i.d.) ×18 cm and the column was washed with 600 ml chloroform/methanol/water (2:3:1,v/v). Then a 2000 ml linear gradient from chloroform/methanol/water (2:3:1,v/v) to chloroform/methanol/0.25M NH$_4$HCO$_3$ (2:3:1, v/v) was applied, the assumed product eluting in a broad peak at the end of the gradient. UV-positive fractions were analyzed on HPTLC with chloroform/methanol/25% ammonia/water (70:58:8:8, v/v or 70:38:8:2, v/v) as developing systems. All fractions contained a UV and P$_i$-positive spot of ACVDP-DG (Rf=0.3 with 70:58:8:8 and Rf=0.1 with 70:38:8:2). Major contaminants were an unidentified P$_i$-positive compound with Rf>5 in both developing systems and phosphatidic acid (Rf=0.3 with 70:58:8:8 and Rf is just above ACVDP-DG(0.1) with 70:38:8:2) All product containing fractions were pooled, evaporated to dryness, lyophilized and extracted (Bligh and Dyer) in order to remove residual ammonium hydrogen carbonate.

The combined chloroform layers were evaporated to dryness and dissolved in 15 ml warm chloroform/methanol/ 25% ammonia/water (70:38:8:2, v/v) as developing system, were pooled, evaporated to dryness, and lyophilized.

The compound has a fatty acid to P$_i$ ratio (Shapiro, B., *Biochem. J.* 53:663 (1953)) of 1.05, confirming the absence of PA.

$E_o$ (at 254 nm(max) in chloroform/methanol/water (2:3:1, v/v)=13,000;

Infrared Analysis (KBr disc method): 1735 cm$^{-1}$, (C=O ester (fatty acid), 1231 cm$^{-1}$, (P=O), 1067 cm$^{-1}$, (P—O—=C), 957 cm$^{-1}$, (P—O—P) and 522 cm$^{-1}$, (P—O—P).

Incubation of rat mitochondria with ACVDP-DG and glycerol-3-phosphate showed that the compound is active as substrate in the biosynthesis of phosphatidylglycerol (PG).

The methods of Example 2 are particularly suitable for guanosine-containing nucleosides or nucleoside analogues that are relatively difficult to solubilize.

EXAMPLE 3

Synthesis of

Acyclovir-Diphosphate(1-O-Octadecyl)Glycerol

To a solution of 40 μmols of acyclovir monophosphate (ACVMP) as the TBA- or TOA- salt, in anhydrous pyridine, 40 or 80 μmol of 1-O-octadecyl, 2-acetyl-glycerol-3-phosphate morpholidate in 2 ml of anhydrous pyridine was added and allowed to react overnight at 60° C. The reaction was stopped by evaporation of the pyridine and extraction of the crude mixture with chloroform, methanol, and 0.1N HCL, according to the method of Bligh and Dyer, Can. J. Biochem., 37:911–917 (1959). ACV-diphosphate (1-O-octadecyl, 2-acetyl)glycerol is purified as described above using a column of Q-Sepharose® eluted with a linear gradient of chloroform/methanol/0.25M NH$_4$HCO$_3$(2:3:1, v/v). The fractions containing pure ACV diphosphate (1-O-octadecyl, 2-acetyl)glycerol were combined and evaporated to dryness. The product was taken up in a small volume of chloroform/methanol (1:1) and treated with methanolic KOH as described by Chang and Kennedy, J. Biol. Chem. 242:617–620 (1967) to remove the 2-acetyl group. The base was neutralized with Dowex-50W® (H$^+$form) cation exchange resin (dry mesh, 200–400) and the product, a white powder, was obtained after lipid extraction by the method of Bligh and Dyer as noted above.

EXAMPLE 4

1-(2'-DEOXY-2'-FLUORO-B-D-ARABINOFURANOSYL)-5-IODOURACIL-5'-DIPHOSPHATE-sn-3-(1,2-DIPALMITOYL) GLYCEROL (FIAU-DP-DPG)

A. Synthesis of 1,2-dipalmitoyl-sn-glycero-3-phosphoromorpholidate:

Dipalmitoylphosphatidic acid (950 mg, 1.47 mmol) was prepared from its disodium salt, essentially as described in Example 1, Part C. Free phosphatidic acid was dissolved in 30 ml chloroform, and the obtained solution was transferred to a two-neck round bottom flask, which contained 30 ml tert-butanol, morpholine (0.53 ml, 6 mmol), and distilled water (0.1 ml, 6 mmol). This mixture was gently refluxed and a solution of dicyclohexylcarbodiimide (1.20 g, 5.9 mmol) in 30 ml tert-butanol was added stepwise from a dropping funnel within 2 hours. The reaction was monitored by thin layer chromatography using silica 60A F254 TLC plates and chloroform/methanol/ammonium hydroxide/water (80:20:1:1 v/v) as eluent (Rf=0.53). The solvent was evaporated under vacuum and the residue was added to 50 ml water. This aqueous suspension was extracted five-times with 75-ml portions of chloroform. The chloroform layers were collected and evaporated to dryness and then lyophilized from cyclohexane three times to yield a white foam. This compound was used without further purification in the subsequent synthesis steps.

B. Synthesis of 1-(2'-deoxy-2'-fluoro-β-D-arabinofuranosyl)-5'-monophosphate (FIAU-MP):

FIAU (800 mg, 2.16 mmol) was dissolved in trimethyl phosphate (2 ml) at 45° C. with vigorous stirring. The reaction mixture was cooled to 0° C. under argon and added phosphorus oxychloride (2 ml, 20 mmol) via syringe. The reaction mixture was first stirred at 0° C. for one hour, and then kept at -20° C. for 12 hours. The reaction was monitored by TLC (acetic acid:n-butanol:water, 1:4:1 v/v). FIAU-MP precipitated as a white crystal. The supernatant was discarded and the precipitate was washed with anhydrous ether (5×10 ml). The precipitate was redissolved in water (20 ml) and washed with chloroform (3×20 ml). The aqueous layers were combined and lyophilized to yield crude FIAU-MP (800 mg, 1.83 mmol, 85% yield).

Analysis:

The HPLC retention time of FIAU-MP was 15.3 min using a 250×4.6 mm, 5 micron Brownlee silica column eluted with hexane:2-propanol:ammonium hydroxide:water (43:57:3:7, v/v).

The compound had an Rf of 0.32 on silica 60A F254 TLC plate eluted with acetic acid:n-butanol:water (1:4:1, v/v).

$UV_{max}$:254 nm (hexane:2-propanol:ammonium hydroxide:water, 43:57:3:7, v/v).

C. Coupling of 1,2-dipalmitoyl-sn-glycero-3-phosphoromorpholidate to 1-(2'-deoxy-2'-fluoro-β-D-arabinofuranosyl)-5-iodouracil-5'-monophosphate (FIAU-DP-DPG 2NH$_4^{3\circ}$):

In a 50 ml round bottom flask, anhydrous 1,2-dipalmitoyl-sn-glycero-3-phosphoromorpholidate (400 mg, 0.55 mmol) and FIAU-MP (200 mg, 0.48 mmol) was dissolved in anhydrous pyridine (15 ml). The solution was evaporated to dryness in vacuum 5-times from anhydrous pyridine, and then 7 ml of anhydrous pyridine were added. This solution was stirred at room temperature overnight under argon. The progress of the reaction was monitored by TLC (chloroform:methanol:ammonium hydroxide:water, 70:38:8:2, v/v). The reaction mixture was then evaporated from toluene (4×10 ml). This residue was dissolved in 15 ml of chloroform:methanol:water (2:3:1, v/v), and acidified to pH 3 with 0.1N hydrochloric acid. Two layers formed, and the aqueous layer was washed with chloroform (2×10 ml). The combined organic layers were evaporated to dryness, and the residue was dissolved in chloroform:methanol:water (2:3:1, v/v) and applied to a DEAE Sephadex (acetate form) column (2.8×30 cm). [DEAE-Sephadex acetate form was washed with 50% aqueous methanol and then methanol prior to packing in chloroform:methanol:water (2:3:1)·] The column was eluted with 250 ml of chloroform:methanol:water (2:3:1, v/v) and then with a linear gradient (1 liter in each reservoir) of 0–0.02 M ammonium acetate made up in the same solvent. Fractions containing the product as judged by TLC were pooled and concentrated to 60 ml. This mixture was extracted with chloroform (5×50 ml), and the organic layer was evaporated to yield FIAU-DP-DPG as the diammonium salt.

Analysis:

The HPLC retention time of FIAU-DP-DPG diammonium salt was 12.65 min. using a 250×4.6 mm, 5 micron Brownlee silica column eluted with hexane:2-propanol:ammonium hydroxide: water (43:57:3:7, v/v) as the developing system.

The compound had an Rf of 0.23 on silica 60A F254 TLC plate eluted with chloroform:methanol:ammonium hydroxide:water (70:28:8:2, v/v).

P: 6.3%, $UV_{max}$: 275 nm, E=5.9×103 (10% methanol in chloroform).

EXAMPLE 4

Synthesis of 1,2-Dimyristoylglycero-3-Phosphate-(pyro)-:Phosphonoformate

A. Synthesis of Phosphatidic Acid Morpholidate:

The sodium salt of dimyristoylphosphatidic acid (DMPA; 25 mg) was dissolved in 5 ml of chloroform and washed twice with 1 ml of 0.1 N HCl. The organic phase was dried over anhydrous sodium sulfate and evaporated under nitrogen. The acid form of DMPA was dissolved in 5 ml of tert-butanol and 1 ml of distilled water. Morpholine (15.2 mg) and dicyclohexylcarbodiimide (DCC) (36 mg) were added to the reaction vessel and refluxed for 5 hr at 90° C. The solvent was removed in vacuo and the residue, representing pure DMPA morpholidate, was purified by thin layer chromatography using 0.5 mm layers of silica gel G developed with chloroform/methanol/ammonia/water (70/30/1/1 by volume), Rf 0.7.

B. Coupling of Phosphonoformic Acid (PFA) And DMPA Morpholidate:

The sodium salt of phosphonoformic acid (PFA) was converted to the acid form by passage through a Dowex AG50W-H+ column (Biorad, Richmond, Calif.). The acid form was lyophilized overnight and 120 mg was added to a reaction vessel which contained DMPA morpholidate (125 mg) dissolved in 5 ml of dry chloroform and 1 ml of dry pyridine. The reaction was sealed under nitrogen and stirred overnight at room temperature. The reaction was stopped by the addition of 10 ml of chloroform/methanol/water (1/2/0.8 by volume) and the chloroform layer was removed after further addition of 2.5 ml each of chloroform and water. The organic (lower) phase was dried over sodium sulfate, evaporated, and purified on silica gel G thin layers developed with a solvent system of chloroform/methanol/20% aqueous methylamine (60/30/10 by volume). The purified product had an Rf of 0.33.

EXAMPLE 5

Synthesis of (3'-Deoxy)Thymidine-5'-Diphosphate-(1,2Dimyristoyl)Glycerol (3dT-DP-DMG)

Dimyristoyl phosphatidic acid morpholidate (DMPA morpholidate) and 3'-deoxythymidine monophosphate (3dTMP) were prepared essentially following the process described in Example 1. In this particular case, 650 µmol DMPA morpholidate was condensed with 350 µmol 3dTMP in 10 ml pyridine. For the synthesis of AZTDP-DG it has been shown that both 2:1 and 1:1 ratios of PA morpholidate and AZT-MP give rise to comparable yields.

Analysis of the reaction course:

At $t_r$=0.5, 1, 1.5, 3, 27, 72, 120 and 168 hours the composition of the reaction mixture was analyzed by HPTLC using silica 60 F254 plates (10×20 cm, upside down) and chloroform/methanol/25% ammonia/water (70:38:8:2, v/v) as developing system. At the indicated time intervals 250 µl of the reaction mixture was withdrawn and the pyridine was removed with a gentle nitrogen stream. The residue was redissolved in chloroform/methanol (1:1, v/v) and this solution was again dried in nitrogen stream. Finally, 250 µl chloroform/methanol (1:1, v/v) was added and the samples were stored at -20° C. until analysis. Aliquots of 5 µl were analyzed simultaneously on HPTLC as described above. The reaction products were visualized by U.V. absorption and spraying with phosphorus reagent. The amount of phosphorus in every spot (FIG. 6: A,B,C,D,E) was quantified using the method of Rouser et al., Lipids 5, 494-496 (1970). Standardization was performed by setting the absolute amount of total $P_i$ at 1000 nmol/analysis (recovery was greater than 80% at all time points).

Figure 6:
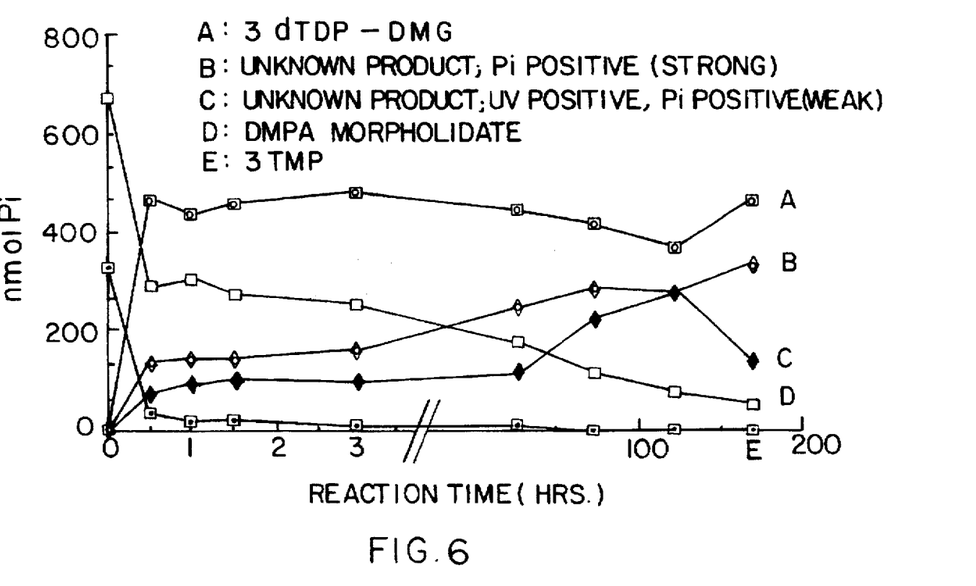
FIG. 6 illustrates the time course of the reaction of 3'-deoxythymidine-monophosphate (3dTMP) with the morpholidate of 1,2-dimyristoyl phosphatidic acid (DMPA morpholidate) as analyzed by determining the phosphorus (Pi) content of the different spots after HPTLC by U.V. absorption.

Results: FIG. 6 illustrates the time course of the reaction as analyzed by $P_i$ content of the different spots:

A=3dTDP-DMG
B=unknown product; $P_i$ positive (strong)
C=unknown product; U.V. positive, $P_i$ positive (weak)
D=DMPA morpholidate
E=3dTMP.

Content of 3dTDP-DMG in the reaction mixture

| Hours | nmol Pi | nmol product | yield % (based on 3dTMP) |
|---|---|---|---|
| 0 | 0 | 0 | 0 |
| 0.5 | 470 | 235 | 71 |
| 1.0 | 440 | 220 | 66 |
| 1.5 | 456 | 228 | 68 |
| 3.0 | 480 | 240 | 72 |
| 27 | 442 | 221 | 66 |
| 72 | 416 | 208 | 63 |
| 120 | 366 | 183 | 55 |
| 168 | 465 | 233 | 70 |

The reaction is essentially completed within 30 minutes as indicated by the amount of 3dTDP-DG formed (A) (71%) and the sharp decrease in the amounts of 3dTMP (E) and DMPA morpholidate (D). As time proceeds, the yield of 3dtDP-DMG does not improve and the amounts of by-products increase as a result of further reaction of DMPA morpholidate (descending curve D, rising curves B and C).

The yields of the syntheses described are between about 50% and 80%, primarily depending on losses in purification. The formation of by-product is controlled by terminating the reaction within a few hours.

The preceding examples can be repeated with similar success by subsituting the generically or specifically described reagents or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of a glyceride di- or triphosphate nucleoside derivative having the formula:

(II)

wherein A is oxygen, sulfur, or methylene $R^1$ and $R^2$ are independently hydroxyl or branched or unbranched aliphatic groups joined through a carbon-carbon, ether, ester, thioether, or thioester linkage and having from 1 to 24 carbon atoms and 0 to 6 sites of unsaturation, k is 0 or 1, and Nu is a nucleoside selected from an adenine guanine, cytosine, uracil, inosine, or thymine moiety linked to a ribose or 2'-deoxyribose 5-carbon cyclic sugar moiety, or a nucleoside analogue selected from:

(1) a purine or pyrimidine base analogue linked to a ribose or 2'-deoxyribose 5-carbon cyclic sugar moiety;

23

(2) a naturally occurring purine or pyrimidine base linked to a ribose analogue; or (3) a purine or pyrimidine base analogue linked to a ribose analogue: wherein said purine or pyrimidine analogue differs from the naturally occurring purine or pyrimidine by substitution, or by deletion or replacement of substituents; and said ribose analogue differs from the naturally occurring ribose by substitution, or deletion or replacement of substituents, by acyclization, or by having a different stereochemistry and salts thereof, comprising the step of:

reacting a phospholipid of Formula (I) as defined in claim 1, with a mono- or diphosphate having the formula (III)

wherein A, Nu, and k, are as hereinabove defined, in a molar ratio of phospholipid:mono- or diphosphate of at least about 1:1 in the presence of a basic catalyst, under anhydrous conditions, whereby said glyceride di- or triphosphate nucleoside is formed, providing that when A is oxygen, and k is O, said phospholipid derivative is not a 1-O-alkyl-2-O-acylglycero-3-phosphate morpholidate when said second compound comprises an adenine, cytosine, 5-fluorouracil, 5-azacytosine, 6-mercaptopurine, or 7-deazaadenine group attached to a pentose which is a ribose or arabinose.

2. The process according to claim 1 wherein the molar ratio of said phospholipid derivative of formula (I) to said compound of formula (III) containing a nucleoside moiety is between about 2:1 and about 1:2.

3. The process according to claim 2 wherein said molar ratio is about 1:1.

4. The process according to claim 1 further comprising the step of purifying the obtained nucleoside diphosphate diglyceride by (a) applying the crude product, in a solution at a pH of about 7, to an HPLC anion exchange column; and (b) eluting the purified product from the column with a solution of a weak base.

5. The process according to claim 4 wherein said purification is performed on a DEAE Sephadex column.

6. The process according to claim 1 wherein Nu is a naturally-occurring ribose, or 2'-deoxyribose, derivative of adenine, guanine, cytosine, uracil, or thymine.

7. The process according to claim 1 wherein Nu is cytidine and the product of said process is a cytidine diphosphate diglyceride.

8. The process according to claim 1 wherein Nu is a nucleoside analogue having a base portion comprising a purine or pyrimidine, and a sugar portion comprising a pentose moiety, wherein at least one said portion is an analogue of a naturally-occurring base or sugar.

9. The process of claim 8 wherein said Nu is 1-(2'-deoxy-2'-fluoro-1-β-arabinosyl)-5-iodocytosine (FIAC); 1-(2'-deoxy-2'-fluoro-1-β-D-arabinofuranosyl)-5-iodouracil (FIAU); 1-(2'deoxy-2'-fluoro-1-β-D-arabinofuranosyl)-5-methyluracil (FMAU); 1-(2'deoxy-2'-fluoro- 1-β-D-arabinofuranosyl)-5-ethyluracil (FEAU); 9-β-D-arabinofuranosyladenine (ara-A); or 1-β-D-arabinofuranosylcytosine (ara-C).

10. The process of claim 8 wherein Nu is an acyclic nucleoside analogue selected from the group consisting of

24

9-(2-hydroxyethoxymethyl)guanine (acyclovir, ACV); and 2-Amino-1,9-((2-hydroxy-1(hydroxymethyl)ethoxy)methyl)-6H-purin-6-one (ganciclovir, GCV).

11. The process according to claim 8 wherein Nu is an nucleoside analogue and the glyceride derivative of said nucleoside analogue is selected from the group consisting of (3'-azido-3'-deoxy)thymidine-5'-diphosphate-(1,2-dilauroyl)glycerol (AZT-DP-DLG);

(3'-azido-3'-deoxy)thymidine-5'-diphosphate-(1,2-dimyristoyl)glycerol (AZT-DP-DMG);

(3'-deoxy)thymidine-5'-diphosphate-(1,2-dilauroyl) glycerol (3DT-DP-DLG);

(3'-deoxy)thymidine-5'-diphosphate-(1,2-dimyristoyl) glycerol (3DT-DP-DMG);

(2',3'-dideoxy)cytidine-5'-diphosphate-(1,2-dilauroyl) glycerol (ddC-DP-DLG);

(2',3'-dideoxy)cytidine-5'-diphosphate-(1,2-dimyristoyl) glycerol (ddC-DP-DMG);

1-(2'-deoxy-2'-fluoro-B-D-arabinofuranosyl)-5-iodouracil-5'-diphosphate-L-(1,2-dipalmitoyl) glycerol (FIAU-DP-DPG);

acyclovir-diphosphate-(1,2-dipalmitoyl)glycerol (ACV-DP-DPG);

acyclovir-diphosphate-(1,2-dimyristoyl)glycerol (ACV-DP-DMG);

acyclovir-diphosphate-(1,O-octadecyl)glycerol and acyclovir-diphosphate-(1-O-hexadecyl)glycerol.

12. A process for the preparation of a phospholipid phosphonoacid derivative having the formula (IV)

wherein

D is a -(CH$_2$)$_m$-C(O)- group;

R$^1$ and R$^2$ are independently hydroxyl or branched or unbranched aliphatic groups joined through a carbon-carbon, ether, ester, thioether, or thioester linkage and having from 1 to 24 carbon atoms and 0 to 6 sites of unsaturation, m is 0 or 1;

k is 0 or 1;

Nu is a nucleoside selected from adenine, guanine, cytosine, uracil, inosine, or thymine moiety linked to a ribose or 2'-deoxyribose 5-carbon cyclic sugar moiety and a nucleoside analogue selected from:

(1) a purine or pyrimidine base analogue linked to ribose or 2'-deoxyribose 5-carbon cyclic sugar moiety;

(2) a naturally occurring purine or pyrimidine base linked to a ribose analogue; or (3) a purine or pyrimidine base analogue linked to a ribose analogue; wherein said purine or pyrimidine analogue differs from the naturally occurring purine or pyrimidine by substitution, or deletion or replacement of substituents; and said ribose analogue differs from the naturally occurring ribose by substitution, or deletion or replacement of substituents, by acyclization, or by having a different stereochemistry; and n is 0 or 1;

and salts thereof, comprising the step of:

reacting a glycerol monophosphate derivative of formula (I), as defined in claim 1, with a phosphonoacid having the formula:

or with the phosphonoacid linked by a carboxyester to Nu and having the formula:

wherein D, k, m, Nu and n are as hereinabove defined, in a molar ratio of phsopholipid:phosphonoacid or its nucleoside derivative of at least about 1:1, in the presence of a basic catalyst, under anhydrous conditions, whereby said phospholipid phosphonoacid derivative is formed.

13. The process of claim 12 wherein the product of said process is a glyceride derivative of said phosphonoacid selected from the group consisting of 1,2-dilauroylglycero-3-phosphate-(pyro)-phosphonoformate; and 1,2-dimyristoylglycero-3-phosphate-(pyro)-phosphonoformate.

14. A process for coupling a phospholipid to a compound having a terminal mono- or diphosphate group, wherein a phospholipid derivative having the formula wherein $R_1$ and $R_2$ are independently hydroxyl or branched or unbranched aliphatic groups joined through a carbon-carbon, ether, ester, thioether, or thioester linkage and having from 1 to 24 carbon atoms and 0 to 6 sites of unsaturation; and L is a leaving group selected from an amine, a diphenyl phosphate or a diphenyl pyrophosphate, is reacted with a second compound having a terminal mono- or diphosphate group, in a molar ratio of phospholipid:second compound of at least about 1:1, in the presence of a basic catalyst, under anhydrous conditions, whereby a glyceride di- or triphosphate derivative is formed; provided that the phospholipid derivative is not a 1-O-alkyl-2-O-acylglycero-3-phosphate morpholidate when said second compound comprises an adenine, cytosine, 5-fluorouracil, 5-azacytosine, 6-mercaptopurine, or 7-deazaadenine group attached to a pentose which is a ribose or arabinose.

15. The process according to claim 14 wherein one or both of $R^1$ and $R^2$ have the structure:

wherein the sum of a, b and c is from 1 to 23, b is 0 to 6, and Y is —C(O)O—, —CH$_2$—O—, —CH=CH—O—, —C(O)S—, —CH$_2$—S—, or —CH=CH—S—.

16. The process according to claim 14 wherein said leaving group is an amino group.

17. The process according to claim 16 wherein said amino group is a morpholino group.

18. The process according to claim 16 wherein said leaving group is an imidazole group.

19. The process according to claim 14 wherein said coupling reaction is performed at a temperature between about 4° C. and about 80° C.

20. The process according to claim 19 wherein said temperature is room temperature.

21. The process according to claim 14 wherein said basic catalyst is pyridine.

22. The process according to claim 21 wherein said reaction is performed in anhydrous pyridine.

23. The process of claim 14, 1, or 12 wherein the reaction time is 72 hours or less.

24. The process of claim 14, 1, or 12 wherein the reaction time is 24 hours or less.

* * * * *